United States Patent [19]

Groll et al.

[11] Patent Number: 4,863,514

[45] Date of Patent: Sep. 5, 1989

[54] MATERIAL FOR FACING DENTURE

[75] Inventors: Werner Groll, Karlstein, Fed. Rep. of Germany; Josef Rothaut, Fort Lee, N.J.

[73] Assignee: Degussa Atiengesellschaft, Frankfurt am Main, Fed. Rep. of Germany

[21] Appl. No.: 308,945

[22] Filed: Feb. 8, 1989

Related U.S. Application Data

[63] Continuation of Ser. No. 836,531, Mar. 5, 1986, abandoned.

[30] Foreign Application Priority Data

Sep. 11, 1985 [DE] Fed. Rep. of Germany ....... 3532329

[51] Int. Cl.$^4$ .......................... A61C 13/00; C22C 1/05
[52] U.S. Cl. ........................................ 75/235; 75/232; 75/247; 428/614; 433/200.1
[58] Field of Search ................ 75/252, 232, 235, 247; 428/614; 433/200.1; 148/430; 419/19

[56] References Cited

U.S. PATENT DOCUMENTS

| | | |
|---|---|---|
| 2,781,579 | 2/1957 | Liebig ............................. 433/200.1 |
| 2,781,580 | 2/1957 | Liebig ............................. 433/200.1 |
| 3,175,904 | 3/1965 | Grant et al. ........................ 75/232 |
| 3,606,766 | 9/1971 | Hill ................................. 75/232 |
| 3,827,891 | 8/1974 | Larry ............................... 75/252 |
| 4,252,558 | 2/1981 | Touboul et al. ..................... 75/252 |
| 4,426,356 | 1/1984 | Nair ................................ 75/247 |
| 4,426,404 | 1/1984 | Shoher et al. ...................... 433/200 |
| 4,476,090 | 10/1984 | Heidsiek ............................ 501/19 |
| 4,689,197 | 8/1987 | Groll et al. ........................ 75/235 |

FOREIGN PATENT DOCUMENTS

| | | | |
|---|---|---|---|
| 22980 | 1/1981 | European Pat. Off. ............. 75/252 |
| 89543 | 5/1985 | Japan .................................... 75/232 |
| 131938 | 7/1985 | Japan .................................... 75/232 |
| 661147 | 11/1951 | United Kingdom ................. 75/232 |
| 935667 | 9/1963 | United Kingdom ................. 75/232 |
| 2082205A | 3/1982 | United Kingdom ................. 75/232 |

*Primary Examiner*—John J. Zimmerman
*Attorney, Agent, or Firm*—Cushman, Darby & Cushman

[57] ABSTRACT

There is provided a material for dentures having metallic matrix, containing 0.5–30 volume % glass having a softening temperature above 650° C. and/or ceramic particles having a maximum grain size of 40 μm.

20 Claims, No Drawings

MATERIAL FOR FACING DENTURE

This is a continuation of application Ser. No. 836,531 filed Mar. 5, 1986, abandoned.

BACKGROUND OF THE INVENTION

This invention is directed to a material which is useful for veneerable dentures having a metallic matrix.

Metallic, veneerable dentures are produced with the lost-wax-method using alloys with a high noble metal content. These alloys have good processability and have an outstanding biocompatibility. However, these alloys are expensive so that in recent years there have been developed alloys having reduced gold and platinum contents and increasing additives of palladium and non-noble metals. These alloys, however, are frequently difficult to process, especially in regard to the melting and casting behavior and solderability. There are likewise used base metal alloys for metallic dentures, but such alloys are even more difficult to process. To veneer these alloys with ceramic, they must be preoxidized in a suitable manner in order to get good adherence of the ceramic to the alloy. Thereby there is not always obtained an optimum oxide layer so that frequently adherence problems occur.

From German OS 3135034 (and related Heidsiek U.S. Pat. No. 4,476,090, the entire disclosure of the Heidsiek U.S. patent being hereby incorporated by reference and relied upon), there is known a material for jewelry and commodities which consist of noble metal with 1 to 70 vol. % glass which must have a transformation temperature of 300° to 500° C. Such materials are not useful as dentures because deformation occurs during the ceramic baking which deteriorates the fit of the denture.

Therefore, it was the problem of the present invention to develop a material for faceable dentures with a metallic matrix which is cheaper than high noble metal containing alloys, which can be processed without problem and which in any case of necessity can be faced reliably and easily with ceramic or synthetic resin.

SUMMARY OF THE INVENTION

This problem was solved according to the invention by including 0.5 to 30 vol. % of glass with a softening temperature above 650° C. and/or ceramic particles having a maximum grain size of 40 μm.

Preferably, the material contains oxidic particles, especially oxidic particles having melting and sintering temperatures which are above the melting respectively sintering temperatures of the metallic components. In particular, there have proven good materials which contain 1 to 12 vol. % of ceramic particles having a particle size ≦5 μm, where noble metal or noble metal mixture is preferably used as matrix component. Of course, the metal matrix can also contain or consist of base metal.

The production of this material is carried out by powder metallurgy by intimately mixing metal powder having a maximum particle size of 100 μm with the ceramic or glass powder condensing the powder mixture and subsequently sintering. The pressing pressure and sintering temperature depend on the metal powders used. It is also possible to prepare the powder mixture as a slip and to sinter the shaped and condensed slip composition after drying.

The incorporation of ceramic or glass powder into the metallic matrix makes it possible that in molding the denture a maximum green density can be achieved. Thus the shrinkage during sintering of the model is mimimized with the fit is improved without reducing the strength.

For an alloy having the composition Au 50 Pt 35 Pd 15 Table 1 shows the influence of the addition of different ceramic powders (in each case 10 vol. %) on the density and the 0.2% yield strength after the linear shrinkage during sintering. It can be seen that the shrinkage is less than in the ceramic free variant although the density in the sintered state is clearly higher in some cases. The 0.2% yield strength increases with one exception through the addition of the ceramic.

In Table 2 there is presented for different powder sizes and for different alloy compositions the influence of $TiO_2$ on the linear shrinkage during and the density after sintering. In this case an increase in density and 0.2% yield strength of the sintered material in the presence of $TiO_2$ is observed too while the shrinkage in most cases is less than that obtained with the corresponding ceramic free variants. These examples show that by the presence of ceramic powders in the metallic matrix there can be attained an increase of the green density.

To produce dentures, for example, there is used a material which consists of 90 vol. % of a metal powder mixture made of 74.4 wt. % gold powder ≦90 μm, 18.6 wt. % gold powder ≦10 μm, and 7 wt.% platinum ≦15 μm with 10 vol.% titanium dioxide which was sintered at 1200° C. However, there are also usable, e.g., the following materials: 50% gold, 35% platinum, 15% palladium, 50% gold, 35% platinum, 10% palladium, 5% silver, or 95% gold, 3% indium, 1% tin.

The compositions can consist of or consist essentially of the stated materials.

TABLE 1

| Metal | Ceramic 10 Vol. % | Powder Size μm | Linear Shrinkage with Sintering at 1200° C., air % | 0.2% Yield Strength MPa | Relative Density Sintered Material % |
|---|---|---|---|---|---|
| 50% Gold 35% Platinum 15% Palladium | — | ≦25 | 21.3 | 582 | 91.8 |
| " | $Bi_2O_3$ | <3 | 21.3 | 610 | 92.3 |
| " | $SnO_2$ | <1 | 17.5 | 415 | 91.6 |
| " | $ZrO_2$ | <20 | 18.8 | 579 | 95.0 |
| " | $TiO_2$ | <5 | 20.0 | 650 | 92.5 |
| " | MgO | <10 | 18.8 | 590 | 93.2 |
| " | Glass Softening Temperature 680° | <20 | 20.5 | 660 | 93.4 |

TABLE 2

| Composition | | | | | | | | | | Properties | | |
| --- | --- | --- | --- | --- | --- | --- | --- | --- | --- | --- | --- | --- |
| Gold | | Platinum | | Palladium | | Silver | | Tin + Indium | | Titanium Dioxide | Linear Shrink- | Rel. Density Sint. Alloy | 0.2% Yield Stre- |
| Concen- tration Wt. % | Particle Size μm | Conc. Wt. % | Par- ticle μm | Conc. Wt. % | Par- ticle μm | Conc. Wt. % | Particle μm | Conc. Wt. % | Particle m | <20 μm Vol. % | age % | % | ngth MPa |
| 50 | ≦25 | 35 | ≦15 | 15 | ≦15 | — | — | — | — | 0 | 21.3 | 91.8 | 582 |
| 50 | ≦25 | 35 | ≦15 | 15 | ≦15 | — | — | — | — | 10 | 20.0 | 92.0 | 610 |
| 50 | ≦25 | 35 | ≦15 | 15 | ≦15 | — | — | — | — | 20 | 18.8 | 91.9 | 650 |
| 50 | ≦50 | 35 | ≦15 | 15 | ≦15 | — | — | — | — | 0 | 20.0 | 91.8 | 630 |
| 50 | ≦50 | 35 | ≦15 | 15 | ≦15 | — | — | — | — | 10 | 20.0 | 97.2 | 692 |
| 50 | ≦100 | 35 | ≦15 | 15 | ≦15 | — | — | — | — | 0 | 20.0 | 92.3 | 625 |
| 50 | ≦100 | 35 | ≦15 | 15 | ≦15 | — | — | — | — | 10 | 18.8 | 93.3 | 620 |
| 50 | ≦50 | 35 | ≦15 | 10 | ≦15 | 5 | ≦15 | — | — | 0 | 17.5 | 84.8 | 550 |
| 50 | ≦50 | 35 | ≦15 | 10 | ≦15 | 5 | ≦15 | — | — | 10 | 17.5 | 90.0 | 580 |
| 95.5 | ≦50 | — | — | — | — | — | — | 4.5 | ≦25 | 0 | 17.6 | 84.7 | 60 |
| 95.5 | ≦50 | — | — | — | — | — | — | 4.5 | ≦25 | 2 | 17.0 | 89.4 | 85 |
| 95.5 | ≦50 | — | — | — | — | — | — | 4.5 | ≦25 | 4 | 17.0 | 91.1 | 95 |

What is claimed is:

1. A denture consisting of the melted or sintered product made from a metallic matrix material consisting of, in addition to the metallic component 0.5 to 30 vol. % of (1) glass having a softening temperature above 650° C. or (2) ceramic oxide particles having a maximum particle size of 40 μm or (3) a mixture of such glass and ceramic oxide particles.

2. A denture according to claim 1 containing ceramic oxide particles.

3. A denture according to claim 2 wherein the oxide is titanium dioxide, bismuth trioxide, tin oxide, zirconium oxide, or magnesium oxide.

4. A denture according to claim 3 wherein the melting and sintering temperatures of the ceramic oxide particles are above the melting and sintering temperatures of the metallic components.

5. A denture according to claim 4 containing 1 to 12 vol.% ceramic oxide particles having a maximum particle size of 5 μm.

6. A denture according to claim 5 wherein the metal matrix consists of noble metal.

7. A denture according to claim 3 containing 1 to 12 vol.% ceramic oxide particles having a maximum particle size of 5 μm.

8. A denture according to claim 7 wherein the metal matrix consists of noble metal.

9. A denture according to claim 2 wherein the melting and sintering temperatures of the ceramic oxide particles are above the melting and sintering temperatures of the metallic components.

10. A denture according to claim 9 containing 1 to 12 vol.% ceramic oxide particles having a maximum particle size of 5 μm.

11. A denture according to claim 8 wherein the metal matrix consists of noble metal.

12. A denture according to claim 2 containing 1 to 12 vol. % ceramic oxide particles having a maximum particle size of 5 μm.

13. A denture according to claim 12 wherein the metal matrix consists of noble metal.

14. A denture according to claim 1 wherein the melting and sintering temperatures of the ceramic oxide particles are above the melting and sintering temperatures of the metallic components.

15. A denture according to claim 14 containing 1 to 12 vol.% ceramic oxide particles having a maximum particle size of 5 μm.

16. A denture according to claim 7 wherein the metal matrix consists of noble metal.

17. A denture according to claim 6 wherein the metal matrix consists of noble metal.

18. A denture according to claim 1 containing 1 to 12 vol.% ceramic oxide particles having a maximum particle size of 5 μm.

19. A denture according to claim 18 wherein the metal matrix consists of noble metal.

20. A denture according to claim 1 wherein the metal matrix consists of noble metal.

* * * * *